United States Patent
Cost

(10) Patent No.: US 10,883,119 B2
(45) Date of Patent: Jan. 5, 2021

(54) METHODS AND COMPOSITIONS FOR DELIVERY OF BIOLOGICS

(71) Applicant: Sangamo BioSciences, Inc., Richmond, CA (US)

(72) Inventor: Gregory J. Cost, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 51 days.

(21) Appl. No.: 13/939,633

(22) Filed: Jul. 11, 2013

(65) Prior Publication Data

US 2014/0017214 A1 Jan. 16, 2014

Related U.S. Application Data

(60) Provisional application No. 61/670,451, filed on Jul. 11, 2012.

(51) Int. Cl.
*C12N 15/90* (2006.01)
*A61K 35/18* (2015.01)
*A61K 38/46* (2006.01)

(52) U.S. Cl.
CPC .......... *C12N 15/907* (2013.01); *A61K 35/18* (2013.01); *A61K 38/465* (2013.01); *C12Y 301/01008* (2013.01)

(58) Field of Classification Search
None
See application file for complete search history.

(56) References Cited

U.S. PATENT DOCUMENTS

| | | | |
|---|---|---|---|
| 5,399,493 A * | 3/1995 | Emerson | C07K 14/5403 435/378 |
| 5,599,705 A * | 2/1997 | Cameron | A61K 38/42 435/378 |
| 5,759,517 A * | 6/1998 | Anderson | A61K 47/6445 424/1.11 |
| 5,760,012 A * | 6/1998 | Kmiec et al. | 514/44 R |
| 5,789,538 A | 8/1998 | Rebar et al. | |
| 5,925,523 A | 7/1999 | Dove et al. | |
| 6,007,988 A | 12/1999 | Choo | |
| 6,013,453 A | 1/2000 | Choo | |
| 6,140,081 A | 10/2000 | Barbas | |
| 6,140,466 A | 10/2000 | Barbas, III et al. | |
| 6,200,759 B1 | 3/2001 | Dove et al. | |
| 6,231,880 B1 * | 5/2001 | Perrine | 424/423 |
| 6,242,568 B1 | 6/2001 | Barbas, III et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,794,136 B1 | 9/2004 | Eisenberg et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,153,949 B2 | 12/2006 | Kim et al. | |
| 7,163,824 B2 | 1/2007 | Cox, III et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,888,121 B2 | 2/2011 | Urnov et al. | |
| 7,951,925 B2 | 5/2011 | Ando et al. | |
| 8,110,379 B2 | 2/2012 | DeKelver et al. | |
| 8,420,782 B2 | 4/2013 | Bonas et al. | |
| 8,440,431 B2 | 5/2013 | Voytas et al. | |
| 2002/0151068 A1 * | 10/2002 | Haley | A61K 48/005 435/456 |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2005/0267061 A1 | 12/2005 | Martin | |
| 2006/0063231 A1 | 3/2006 | Li et al. | |
| 2006/0188987 A1 | 8/2006 | Guschin et al. | |
| 2006/0253913 A1 | 11/2006 | Jin et al. | |

(Continued)

FOREIGN PATENT DOCUMENTS

GB 2338237 A 12/1999
WO 1988/08450 A1 11/1988

(Continued)

OTHER PUBLICATIONS

Visigalli et al. Gene Therapy Augments the Efficacy of Hematopoietic Cell Transplantation and Fully Corrects Mucopolysaccharidosis Type I Phenotype in the Mouse Model. Blood. 2010. 116:5130-5139.*
GenBank Accession No. M1357.1.*
GenBank Accession No. 15182.1.*
Cox, Timothy M. Gaucher Disease: Clinical Profile and Therapeutic Developments. Biologics: Targets & Therapy, 2010. 4:299-313.*
Bouhassira, Eric E. Concise Review: Production of Cultured Red Blood Cells from Stem Cells. Stem Cells Translational Medicine, 2012. 1: 927-933. Available online Nov. 26, 2012.*

(Continued)

*Primary Examiner* — Christopher M Babic
*Assistant Examiner* — Kimberly A. Aron
(74) *Attorney, Agent, or Firm* — Pasternak Patent Law

(57) ABSTRACT

Nucleases and methods of using these nucleases for genetic alteration of red blood cells (RBCs), for example for providing for a protein lacking in a monogenic disorder or a biologic for the treatment of exposure to a toxin using genetically altered RBCs.

6 Claims, No Drawings

Specification includes a Sequence Listing.

(56) References Cited

U.S. PATENT DOCUMENTS

| | | | |
|---|---|---|---|
| 2007/0111279 A1* | 5/2007 | Rosenberg | C12N 9/18 435/69.1 |
| 2007/0134796 A1* | 6/2007 | Holmes | A61K 48/0008 435/455 |
| 2007/0218528 A1 | 9/2007 | Miller | |
| 2008/0131962 A1 | 6/2008 | Miller | |
| 2008/0159996 A1 | 7/2008 | Ando et al. | |
| 2008/0299580 A1 | 12/2008 | DeKelver et al. | |
| 2008/0317732 A1* | 12/2008 | Hersh | A61K 48/00 424/94.63 |
| 2009/0068164 A1 | 3/2009 | Barbas et al. | |
| 2009/0156534 A1* | 6/2009 | Lisowski | A61K 31/7088 514/44 R |
| 2009/0285892 A1* | 11/2009 | Sakthivel | B82Y 5/00 424/484 |
| 2010/0041014 A1* | 2/2010 | Hyde et al. | 435/5 |
| 2010/0047805 A1 | 2/2010 | Wang | |
| 2010/0218264 A1 | 8/2010 | Cui et al. | |
| 2010/0229252 A1* | 9/2010 | Perez-Michaut | C07K 14/805 800/13 |
| 2011/0041195 A1 | 2/2011 | Doyon | |
| 2011/0201055 A1 | 8/2011 | Doyon et al. | |
| 2011/0207221 A1 | 8/2011 | Cost et al. | |
| 2011/0265198 A1 | 10/2011 | Gregory et al. | |
| 2011/0281361 A1 | 11/2011 | DeKelver et al. | |
| 2011/0287512 A1 | 11/2011 | Paschon et al. | |
| 2011/0294114 A1 | 12/2011 | Van Der Loo et al. | |
| 2011/0301073 A1 | 12/2011 | Gregory et al. | |
| 2012/0017290 A1 | 1/2012 | Cui et al. | |
| 2013/0122591 A1 | 5/2013 | Cost et al. | |
| 2013/0137104 A1 | 5/2013 | Cost et al. | |
| 2013/0177960 A1 | 7/2013 | Rebar | |
| 2013/0177983 A1 | 7/2013 | Rebar | |
| 2013/0326645 A1 | 12/2013 | Cost et al. | |

FOREIGN PATENT DOCUMENTS

| | | |
|---|---|---|
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | 2003002155 A1 | 1/2003 |
| WO | WO 03/016496 A2 | 2/2003 |
| WO | WO 2007/014275 A2 | 2/2007 |
| WO | WO 2009/042163 A2 | 4/2009 |
| WO | WO 2009/054985 A1 | 4/2009 |
| WO | WO 2010/079430 A1 | 7/2010 |
| WO | 2010/125471 A2 | 11/2010 |
| WO | 2011100058 A1 | 8/2011 |
| WO | WO 2013/044008 A2 | 3/2013 |

OTHER PUBLICATIONS

Chang et al. Stem Cell-Derived Erythroid Cells Mediate Long-term Systemic Protein Delivery, Nature Biotechnology, 2006. 24(8) 1017-1021.*
Barranger et al., "Gene Transfer Approaches to the Lysosomal Storage Disorders," Neurochemical Research 24(4):601-615 (1999).
Bernhard et al., "Idenification of Hematopoietic Stem-Cell Specific miRNAs Enables Gene Therapy of Goboid Cell Leukodystrophy," Science Translational Medicine 2(58):66-76 (2010).
Biffi et al., "Genetically-Modified Hematopoietic Stem Cells and Their Progeny for Widespread and Efficient Protein Delivery to Diseased Sites: The Case of Lysosomal Storage Disorders," Current Gene Therapy 12(5):38-388 (2012).
Biffi et al., "Metachromatic Leuodystrophy: An Overview of Current and Prospective Bone Marrow Treatments," Transplantation 42(2):S2-S6 (2008).
Gritti et al., "Gene Therapy for Lysosomal Storage Disorders," Expert Opinion on Biological Therapy 11(9):1153-1167 (2011).
Hofling et al., "Human CD34+ Hematopoietic Progenitor Cell-Directed Lentiviral-Mediated Gene Therapy in a Xenotransplantation Model of Lysosomal Storage Disease," Molecular Therapy: The Journal of the American Society of Gene Therapy 9(6):856-865 (2004).
Kim et al., "Long-Term Expression of the Human Glucocerebrosidase Gene In Vivo After Transplantation of Bone-Marrow-Derived Cells Transformed With a Lentivirus Vector," Journal of Gene Medicine 7(7):878-887 (2005).
Leimig et al., "Functional Amelioration of Murine Galactosialidosis by Genetically Modified Bone Marrow Hematopoietic Progenitor Cells," Blood 99(9):3169-3178 (2002).
Muzykantov, "Drug Dlivery by Red Blood Cells: Vascular Carriers Designed by Mother Nature," Expert Opinion on Drug Delivery 7(4):403-427 (2010).
Neik et al., "Lentiviral Gene Therapy of Murine Hematopoietic Stem Cells Ameliorates the Pompe Disease Phenotype," Blood 115(26):5329-5337 (2010).
Papapetrou et al., "Genomic Safe Harbors Permit High [Beta]-Globin Transgene Expression in Thassemia Induced Pluripotent Stem Cells," Nature Biotechnology 29(1):73-78 (2011).
Ramsubir et al., "In Vivo Delivery of Human Acid Ceramidase via Cord Blood Transplantation and Direct Injection of Lentivirus as Novel Treatment Approaches for Farber Disease," Molecular Genetics and Metabolism 95(3):133-141 (2008).
Wang et al., "Reprogramming Erythroid Cells for Lysosomal Enzyme Production Leads to Visceral and CNS Cross-Correction in Mice With Hurler Syndrome," PNAS USA 106(47):19958-19963 (2009).
Wang et al., "Genetic Correction of [Beta]-Thalassemia Patient-Specific IPS Cells and Its Use in Improving Hemoglobin Production in Irradiated SCID Mice," Cell Research 22(4):637-648 (2012).
Wenfang et al., "Chapter Two—Precision Editing of Large Animal Genomes," Advances in Genetics 80(1):37-97 (2012).
Zhou et al., "Functional Amelioration of Murine Galactosialidosis by Geneticially Modified Bone Marrow Hematopoietic Progenitor Cells," Blood 99(9):3169-3178 (2002).
Beerli, et al., "Engineering Polydactyl Zinc-Finger Transcription Factors," *Nature Biotechnol.* 20:135-141(2002).
Boch, et al., "Breaking the Code of DNA Binding Specificity of TAL-Type III Effectors," *Science* 326:1509-1512 (2009).
Bonas, et al., "Genetic and Structural Characterization of the Avirulence Gene AVRBS3 From Xanthomonas Campestris Pv. Vesicatoria," *Mol. Gen. Genet.* 218:127-136 (1989).
Broomfield, et al., "Protection by Butyrylcholinesterase Against Organophosphorus Poisoning in Nonhuman Primates," *Pharmacol. Exp. Ther.* 259(2):633-638 (1991).
Brouns, et al., "Small CRISPR RNAs Guide Antiviral Defense in Prokaryotes," *Science* 321:960-964 (2008).
Choo, et al., "Advances in Zinc Finger Engineering," *Curr. Opin. Struct. Biol.* 10:411-416 (2000).
Cong, et al., "Multiplex Genome Engineering Using CRISPR/CAS Systems," *Science* 339(6121):819-823; DOI: 10.1126/science.1231143 (2013).
Goode, et al., "The Repetitive DNA Elements Called CRISPRs and Their Associated Genes: Evidence of Horizontal Transfer Among Prokaryotes," *J. Mol. Evol.* 62:718-729 (2006).
Gupta, et al., "Directed Evolution of Hydrolases for Prevention of G-Type Nerve Agent Intoxication," *Nat. Chem. Biol.* 7(2):120-125 (2011).
Guschin, et al., "A Rapid and General Assay for Monitoring Endogenous Gene Modification," *Methods Mol. Biol.* 649:247-256 (2010).
Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).

(56) References Cited

OTHER PUBLICATIONS

Hale, et al., "Prokaryotic Silencing (PSI)RNAs in Pyrococcus Furiosus," *RNA* 14:2572-2579 (2008).
Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007).
Hwang, et al., "Efficient Genome Editing in Zebrafish Using a CRISPR-CAS System," *Nature Biotechnology* 31(3):227 (2013).
Isalan, et al., "A Rapid, Generally Applicable Method to Engineer Zinc Fingers Illustrated by Targeting the HIV-1 Promoter," *Nat. Biotechnol.* 19:656-660 (2001).
Jansen, et al., "Identification of Genes That Are Associated With DNA Repeats in Prokaryotes," *Molecular Microbiology* 43(6):1565-1575 (2002).
Jinek, et al., "A Programmable Dual-RNA-Guided DNA Endonuclease in Adaptive Bacterial Immunity," *Science* 337:816-821 (2012).
Kay, et al., "A Bacterial Effector Acts as a Plant Transcription Factor and Induces a Cell Size Regulator," *Science* 318:648-651 (2007).
Kim, et al., "Hybrid Restriction Enzymes: Zinc Finger Fusions to FOK I Cleavage Domain," *PNAS USA* 93(3):1156-1160 (1996).
Kormann, et al., "Expression of Therapeutic Proteins After Delivery of Chemically Modified MRNA in Mice," *Nature Biotechnology* 29(2):154-157 (2011).
Lei, et al., "Repurposing CRISPR as an RNA-Guided Platform for Sequence-Specific Control of Gene Expression," *Cell* 152(5):1173-1183 (2013).
Lenz, et al., "Stoichiometric and Catalytic Scavengers as Protection Against Nerve Agent Toxicity: A Mini Review," *Toxicology* 233(1-3):31-39 (2007).
Lillestol, et al., "A Putative Viral Defence Mechanism in Archaeal Cells," *Archaea* 2:59-72 (2006).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).
Makarova, et al., "A DNA Repair System Specific for Thermophilic Archaea and Bacteria Predicted by Genomic Context Analysis," *Nucleic Acids Res.* 30:482-496 (2002).
Moscou, et al., "A Simple Cipher Governs DNA Recognition by TAL Effectors," *Science* 326:1501 (2009).

Pabo, et al., "Design and Selection of Novel CYS2HIS2 Zinc Finger Proteins," *Ann. Rev. Biochem.* 70:313-340 (2001).
Perez, et al., "Establishment of HIV-1 Resistance in CD4+ T Cells by Genome Editing Using Zinc-Finger Nucleases," *Nature Biotechnology* 26(7):808-816 (2008).
Qi, et al., "Repurposing CRISPR as an RNA-Guided Platform for Sequence-Specific Control of Gene Expression," *Cell* 152:1173-1183 (2013).
Roberts, et al., "REBASE: Restriction Enzymes and Methyltransferases," *Nucleic Acid Research* 31:418-420 (2003).
Samantaray, et al., "Calpain as a Potential Therapeutic Target in Parkinson's Disease," *CNS Neural. Disord. Drug Targets* 7(3):305-312 (2008).
Schornack, et al., "Gene-For-Gene-Mediated Recognition of Nuclear-Targeted AVRBS3-Like Bacterial Effector Proteins," *J. Plant Physiol.* 163(3):256-272 (2006).
Segal, et al., "Custom DNA-Binding Proteins Come of Age: Polydactyl Zinc-Finger Proteins," *Curr. Opin. Biotechnol.* 12:632-637 (2001).
Sorek, et al., "CRISPR—A Widespread System That Provides Acquired Resistance Against Phages in Bacteria and Archaea," *Nat. Rev. Microbiol.* 6:181-186 (2008).
Tang, et al., "Identification of 86 Candidates for Small Non-Messenger RNAs From the Archaeon *Archaeoglobus fulgidus*," *Proc. Natl. Acad. Sci.* 99:7536-7541 (2002).
Tang, et al., "Identification of Novel Non-Coding RNAs as Potential Antisense Regulators in the Archaeon *Sulfolobus solfataricus*," *Mol. Microbiol.* 55:469-481 (2005).
Tatusov, et al., "A Genomic Perspective on Protein Families," *Science* 278:631-637 (1997).
Tatusov, et al., "The COG Database: An Updated Version Includes Eukaryotes," *BMC Bioinformatics* 4(1):41 (2003).
Urnov, et al., "Highly Efficient Endogenous Human Gene Correction Using Designed Zinc-Finger Nucleases," *Nature* 435(7042):646-651 (2005).
Vaziri, "Mechanisms of Lead-Induced Hypertension and Cardiovascular Disease," *Am. J. Physiol. Heart Circ. Physiol.* 295(2):H454-H465 (2008).
Ragno, et al., "Salvaging of Liquid-Preserved O-Positive and O-Negative Red Blood Cells by Rejuvenation and Freezing," Transfusion and Apheresis Science, 35(2):137-43 (2006).
Zhou, et al., "Mouse Model for the Lysosomal Disorder Galactosialidosis and Correction of the Phenotype With Overexpressing Erythroid Precursor Cells," Genes & Development 9(21):2623-2634 (1995).

* cited by examiner

SEQUENCE LISTING

```
<160> NUMBER OF SEQ ID NOS: 27

<210> SEQ ID NO 1
<211> LENGTH: 15
<212> TYPE: DNA
<213> ORGANISM: Homo sapiens

<400> SEQUENCE: 1
gcagtaacgg cagac                                                          15

<210> SEQ ID NO 2
<211> LENGTH: 16
<212> TYPE: DNA
<213> ORGANISM: Homo sapiens

<400> SEQUENCE: 2
gggcaaggtg aacgtg                                                         16

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Arg Ser Asn Leu Ser Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Gly Asp Leu Thr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Asp Thr Leu Ser Gln
1               5

<210> SEQ ID NO 6
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Gly Ser Leu Thr Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Asn Ala Thr Arg Ile Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Asp Ser Leu Ser Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ser Ser Asn Arg Lys Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Ala Ala Leu Ser Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

```
Arg Leu Asp Asn Arg Thr Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Ser His Leu Ser Arg
1               5

<210> SEQ ID NO 13
<211> LENGTH: 16
<212> TYPE: DNA
<213> ORGANISM: Homo sapiens

<400> SEQUENCE: 13
ggagaagtct gccgtt                                                       16

<210> SEQ ID NO 14
<211> LENGTH: 18
<212> TYPE: DNA
<213> ORGANISM: Homo sapiens

<400> SEQUENCE: 14
agtcaggtgc accatggt                                                     18

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ser Gly Ser Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Ser Asp Leu Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Arg Ser Ala Leu Ala Arg
1               5
```

```
<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Ser Asn Leu Ala Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Gly His Leu Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Arg His His Leu Thr Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Arg His Asn Leu Arg Ala
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Gln Ser Asn Leu Arg Ala
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 23

Arg Asn Ala Ser Arg Thr Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Asp Asn Leu Ser Glu
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Gln His Arg Lys Thr
1               5

<210> SEQ ID NO 26
<211> LENGTH: 9
<212> TYPE: PRT
<213> ORGANISM: Unknown
<220> FEATURE:
<223> OTHER INFORMATION: Description of Unknown: "LAGLIDADG" family
      peptide motif sequence

<400> SEQUENCE: 26

Leu Ala Gly Leu Ile Asp Ala Asp Gly
1               5

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any hydrophobic amino acid
<220> FEATURE:
<221> NAME/KEY: MOD_RES
<222> LOCATION: (4)..(8)
<223> OTHER INFORMATION: Any amino acid
<220> FEATURE:
<221> NAME/KEY: MOD_RES
<222> LOCATION: (10)..(10)
<223> OTHER INFORMATION: Any hydrophobic amino acid
<220> FEATURE:
<223> OTHER INFORMATION: See specification as filed for detailed
      description of substitutions and preferred embodiments

<400> SEQUENCE: 27

Gly Xaa Gly Xaa Xaa Xaa Xaa Xaa Gly Xaa Gly
1               5                   10
```

METHODS AND COMPOSITIONS FOR DELIVERY OF BIOLOGICS

CROSS-REFERENCE TO RELATED APPLICATIONS

The present application claims the benefit of U.S. Provisional Application No. 61/670,451, filed Jul. 11, 2012, the disclosure of which is hereby incorporated by reference in its entirety.

TECHNICAL FIELD

The present disclosure is in the fields of genetic engineering of red blood cells, including for the therapeutic delivery of biologics to tissues especially for the treatment of exposure to a toxin.

BACKGROUND

Gene therapy holds enormous potential for a new era in human medicine. These methodologies will allow treatment for conditions that heretofore have not been addressable by standard medical practice. One area that is especially promising is the ability to add a transgene to a cell to cause that cell to express a product previously not being produced in that cell. Examples of uses of this technology include the insertion of a gene encoding a novel therapeutic protein, insertion of a coding sequence encoding a protein that is lacking in the cell or in the individual, and insertion of a sequence that encodes a structural nucleic acid such as a microRNA or siRNA.

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., co-owned U.S. Pat. No. 7,888,121). Nucleases, such as zinc finger nucleases (ZFNs), transcription activator-like effector nucleases (TALENs), or nuclease systems such as the CRISPR/Cas system (utilizing an engineered guide RNA), specific for targeted genes can be utilized such that the transgene construct is inserted by either homology directed repair (HDR) or by end capture during non-homologous end joining (NHEJ) driven processes.

Targeted loci include "safe harbor" loci such as the AAVS1 and CCR5 genes in human cells, and Rosa26 in murine cells (see, e.g., co-owned United States Patent Publication Nos. 20080299580; 20080159996 and 201000218264). Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

While delivery of the transgene to the target cell is one hurdle that must be overcome to fully enact this technology, another issue that must be conquered is insuring that after the transgene is inserted into the cell and is expressed, the gene product so encoded must reach the necessary location with the organism, and be made in sufficient local concentrations to be efficacious. For diseases characterized by the lack of a protein or by the presence of an aberrant non-functional one, delivery of a transgene encoded wild type protein can be extremely helpful in ameliorating, treating and/or preventing conditions, for example, expression of a transgene for the treatment of genetic diseases (e.g. a lysosomal storage disease).

Red blood cells (RBCs), or erythrocytes, are the major cellular component of blood. In fact, RBCs account for one quarter of the cells in a human. In humans mature RBCs lack a nucleus and many other organelles, and are full of hemoglobin to facilitate their job of taking oxygen from the lungs and delivering it to the peripheral tissues. RBCs are developed in the bone marrow from CD34+ hematopoietic stem cells and have a half-life of approximately 100 to 120 days. RBCs have protein antigens on their surfaces (agglutinogens) which account for blood type (A, B, AB or O) that can be problematic if a subject is transfused with donor blood that is an incompatible blood type. The second most significant type of blood cell antigens are the Rh (Rhesus) antigens, comprising approximately 50 different antigens. The gene encoding the O antigen has been naturally mutated to non-functionality long ago such that type O, Rh(−) blood can be used to donate to anyone since none of the major blood type antigens will be present. In addition, another set of blood cell antigens are the Kell antigens encoded by the KEL gene. Kell is a type II transmembrane glycoprotein that is highly polymorphic and some individuals develop anti-Kell antibodies following transfusion.

Exposure to toxins, via industrial accidents, long term exposure from accumulated toxins in the environment, or chemical warfare is an ongoing concern. Chemical warfare, which involves the use of non-living toxins such as botulinum toxin, ricin, and saxitoxin, is different from the use of conventional weapons or nuclear weapons because the destructive effects of chemical weapons are not primarily due to any explosive force. About 70 different chemicals have been used or stockpiled as chemical warfare agents during the 20th century, including various nerve agents, a class of phosphorous-containing organic chemicals that disrupt the mechanism by which nerves transfer messages to organs, such as Cyclosarin, Sarin, Soman, Tabun, VX, VR; insecticides and Novichok agents. Toxic chemicals can also be released into the environment dues to industrial accidents such as the incident in Bhopal, India where the gas methyl isocyanate was released resulting in the exposure of hundreds of thousands of people, and the death of thousands.

Nerve disruption as a result of exposure to these agents is caused by the covalent modification of the active site of acetylcholinesterase, an enzyme that normally relaxes the activity of acetylcholine, a neurotransmitter. Exposure to nerve agents produces a multitude of symptoms, ultimately resulting in death by asphyxiation. Classified as weapons of mass destruction by the United Nations, U.S. troops were exposed to nerve agents during the first Gulf War; and the nerve agent Sarin was released in a 1995 terrorist attack in Japan. Due to the nerve agents' skin permeability, full-body protection is required in addition to a respirator, equipment not well-suited for soldiers or first-responders. While treatment options exist, prophylaxis is poor. One strategy involves the use of pyridostigmine, a small molecule that is able to reversibly bind in the acetylcholinesterase active site, but this is not an ideal solution. After associating with the enzyme, the pyridostigmine only stays in the active site for a period of hours, so for prophylactic use, it must be taken every 8 to 12 hours. Additionally, it cannot cross the blood brain barrier and so is only effective in the peripheral nervous system and has other non-desirous side effects. Other small molecule compounds such as atropine, oximes, and combinations with anti-convulsives such as diazepam are used but have limited efficacy (see Russell et al (2003) *Annu Rev Biomed Eng* 5:1-27).

Butyrylcholinesterase (BCHE) is a naturally occurring protein in human serum and is a target for a broad spectrum of organophosphate nerve agents (see Broomfield et al. (1991) *Pharmacol Exp Ther.* 259(2):633-8). Recombinant BCHE is under development as a sacrificial prophylactic nerve agent countermeasure to block the action and effects of nerve agents (see Lenz et al, (2007) *Toxicology.* 233(1-3):31-9). Catalytic analogs of BCHE are under earlier-stage development. Another enzyme, serum paraoxonase/arylesterase 1 (PON1) has been engineered to also degrade some nerve agents (see Gupta et al. (2011) Nat Chem Biol. 7(2):120-5. Epub 2011 Jan. 9). Other helpful fusion partners can be carboxylesterases (CaEs), antibodies, and cholinesterases (ChEs), including fetal bovine serum AChE (FBS-AChE), equine serum butyrylcholinesterase (EqBChE), and phosphotriesterase from. Pseudonomas *diminuta*. While an attractive protective option, the short half-life and high cost of injectable recombinant proteins may limit the usefulness of recombinant BCHE or engineered PON1 in standard practice.

The recognition of potential dangers of environmental toxins has increased in recent years. Toxins in our environment include compounds such as heavy metals (e.g. lead, cadmium), polychlorinated biphenyls (PCBs), dioxins, pesticides, phthalates, asbestos, and halogens (chlorine, fluorine) are potentially associated with many diseases such as cancer, hypertension, cardiovascular disease, Parkinson's disease, lung disease, mental retardation, and osteoporosis (see for example Vaziri (2008) *Am J Physiol Heart Circ Physiol.* 295(2): H454-H465, Samantaray et al. (2008) *CNS Neurol Disord Drug Targets.* 7(3):305-12). These toxins often play initiating roles in these diseases or interact with disease initiators to accelerate disease progression.

Thus, there remains a need for additional methods and compositions that can be used to deliver an expressed transgene encoded gene product at a therapeutically relevant level, for example to treat exposure to environmental, industrial and chemical warfare toxins such as nerve gases and genetic conditions such as lysosomal storage diseases.

SUMMARY

Disclosed herein are methods and compositions for genetic alteration of red blood cells, for example to deliver a therapeutic biologic (e.g., protein) to the desired site within an organism with a genetic condition (e.g., lysosomal storage disease) and/or an organism that has been exposed or will be exposed to a toxin. The invention describes the alteration of a red blood cell such that it produces high levels of the therapeutic to protect or treat an exposed subject (e.g., human patient), with the introduction of a population of these altered RBCs into the subject to supply that needed therapeutic. The therapeutic biologic provides a protein (e.g., therapeutic protein), for example that replaces the function of a mutant protein in a genetic disease and/or blocks the effect of, degrades and/or detoxifies a toxin.

In one aspect, described herein is a zinc-finger protein (ZFP) that binds to target site in a region of interest (e.g., a globin or safe harbor gene) in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the zinc finger domain recognizes a target site in a globin or safe harbor gene. In certain embodiments, the zinc finger domain comprises 5 zinc finger domains and recognizes a target site in a globin gene (e.g., a zinc finger protein having 5 fingers with the recognition helix regions shown in Table 3).

In another aspect, described herein is a TALE protein (Transcription activator like) that binds to target site in a region of interest (e.g., a globin or safe harbor gene) in a genome, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the TALE DNA binding domain recognizes a target site in a globin or safe harbor gene.

In another aspect, described herein is a CRISPR/Cas system that binds to target site in a region of interest (e.g., a highly expressed gene, a disease associated gene or a safe harbor gene) in a genome, wherein the CRISPR/Cas system comprises a CRIPSR/Cas nuclease and an engineered crRNA/tracrRNA (or single guide RNA). In certain embodiments, the CRISPR/Cas system recognizes a target site in a highly expressed, disease associated, or safe harbor gene. In certain embodiments, the CRISPR/Cas system recognizes a target in a globin, albumin, CCR5, CXCR4, AAVS1, Rosa, or HPRT gene.

The ZFN, TALEN, and/or CRISPR/Cas system as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the ZFN, TALEN, and/or CRISPR/Cas system binds to and/or cleaves a globin gene. In other embodiments, the ZFN, TALEN, and/or CRISPR/Cas system binds to and/or cleaves a safe-harbor gene, for example a CCR5 gene, a CXCR4 gene, a PPP1R12C (also known as AAVS1) gene, an albumin gene or a Rosa gene. See, e.g., U.S. Patent Publication Nos. 20080299580; 20080159996; 201000218264; 20110301073; 20130177983; 20130177960 and 20150056705. In addition, to aid in selection, the HPRT locus may be used (see U.S. Patent Publication No. 20130122591). In another aspect, described herein are compositions comprising one or more of the zinc-finger and/or TALE nucleases or CRISPR/Cas system as described herein.

In another aspect, described herein is a polynucleotide encoding one or more ZFNs and/or TALENs or CRISPR/Cas system described herein. The polynucleotide may be, for example, mRNA. In some aspects, the mRNA may be chemically modified (See e.g. Kormann et al, (2011) *Nature Biotechnology* 29(2):154-157).

In another aspect, described herein is a ZFN and/or a TALEN or CRISPR/Cas system expression vector comprising a polynucleotide, encoding one or more ZFNs, TALENs and/or CRISPR/Cas systems described herein, operably linked to a promoter. In one embodiment, the expression vector is a viral vector. In another embodiment, the expression vector is used for the in vitro production of mRNAs encoding the ZFNs, TALENs or CRISPR/Cas systems proteins.

In another aspect, described herein is a genetically modified host cell, such as a red blood cell (RBC) or an RBC precursor cell (stem cell), for example a host cell comprising one or more transgenes. In certain embodiments, the transgene(s) encode(s) a protein that is lacking or not sufficiently functioning in a subject with a genetic condition, for example a lysosomal storage disease (see, Table 2). In other embodiments, the transgene(s) encode(s) one or more polypeptides that degrade, detoxify and/or block the action of a toxin (e.g., nerve agent), for example by encoding a carboxylesterase (CaE), an antibody, a cholinesterase (ChE) such as butyrylcholinesterase (BCHE), fetal bovine serum AChE (FBS-AChE), equine serum butyrylcholinesterase (EqBChE), an arylesterase (e.g., serum paraoxonase/arylesterase 1 (PON1)) and/or phosphotriesterase from *Pseudonomas diminuta*. In some embodiments, the transgenes encode a functional polynucleotide such as an miRNA, shRNA or the like. In certain embodiments, the transgenes are integrated into the genome of the RBC precursor using a nuclease, for example a ZFN, a TALEN (and/or polynucleotide encoding the ZFN and/or TALENs) or CRISPR/Cas system. The host cell may be stably transformed or transiently transfected or a combination thereof with one or more ZFN or TALEN expression vectors or CRISPR/Cas system. In another embodiment, the host cell is treated with mRNAs encoding the nucleases of the invention. In certain embodiments, the nuclease-modified RBC precursors are then expanded and induced to differentiate into a mature RBCs ex vivo. The resulting RBCs can then be administered to a subject, for example for treatment and/or prevention of a condition (e.g., exposure to a toxin such as a nerve agent). In other aspects, the RBC precursors (stem cells) are given in a bone marrow transplant and the RBCs differentiate and mature in vivo. The nucleases may be engineered with specificity to a safe harbor locus, or may have specificity for a gene that is highly expressed in red blood cells. By way of non-limiting example only, the safe harbor locus may be the AAVS1 site, the CCR5 gene or the HPRT gene. By way of non-limiting example only, a gene that is highly expressed in red blood cells is beta globin.

In another aspect, described herein is a method for cleaving a beta globin or safe harbor gene in a cell, the method comprising: introducing, into the cell, one or more polynucleotides encoding one or more ZFNs and/or TALENs or CRISPR/Cas systems that bind to a target site in the one or more globin genes under conditions such that the ZFN(s), TALENs or CRISPR/Cas systems is (are) expressed and the one or more globin or safe harbor genes are cleaved. In certain embodiments, the zinc finger domain comprises 5 zinc finger domains and recognizes a target site in a globin gene (e.g., a zinc finger protein having 5 fingers with the recognition helix regions shown in Table 3). In some embodiments, the polynucleotides comprising the nucleases of the invention comprise expression vectors and in other embodiments, the polynucleotides comprise mRNAs. In other aspects, a genomic sequence in any target gene is replaced, for example using a ZFN or TALEN (and/or vector encoding said ZFN or TALEN) or CRISPR/Cas system as described herein and a "donor" sequence that is inserted into the gene following targeted cleavage with the ZFN, TALEN, and/or CRISPR/Cas system. The donor sequence may be present in the ZFN or TALEN vector, present in a separate vector (e.g., Ad or LV vector) or, alternatively, may be introduced into the cell using a different nucleic acid delivery mechanism. Such insertion of a donor nucleotide sequence into the target locus (e.g., globin gene, other safe-harbor gene, etc.) results in the expression of the transgene under control of the target locus's (e.g. globin's) genetic control elements. In some aspects, insertion of the transgene of interest, for example into a globin gene results in expression of an intact exogenous protein sequence and lacks any globin encoded amino acids. In other aspects, the expressed exogenous protein is a fusion protein and comprises amino acids encoded by the transgene and by additional (e.g., globin) gene sequences (e.g., from the endogenous target locus or, alternatively from globin-encoding sequences on the transgene). In some instances, the globin gene is a beta globin. In other instances, the globin gene is a gamma globin gene. In some instances, the globin sequences will be present on the amino (N)-terminal portion of the exogenous protein, while in others, the globin sequences will be present on the carboxy (C)-terminal portion of the exogenous protein. In other instances, globin sequences will be present on both the N- and C-terminal portions of the exogenous protein. The globin sequences may include full-length wild-type or mutant globin sequences or, alternatively, may include partial globin amino acid sequences. In some embodiments, the globin-transgene fusion is located at the endogenous locus within the cell while in other embodiments, the globin-transgene coding sequence is inserted into a safe harbor within a genome. In some aspects, the safe harbor is selected from the AAVS1, Rosa, HPRT, albumin or CCR5 locus (see co-owned US Patent Publications Nos. 20080299580; 20080159996; 201000218264; 20130122591; and 20130177960 and 20130177960).

In some embodiments, the transgene is expressed such that a therapeutic protein product is retained within the mature red blood cell. In other embodiments, the transgene is fused to the extracellular domain of a membrane protein such that upon expression, a transgene fusion will result in the surface localization of the therapeutic protein. In some aspects, the extracellular domain is chosen from those proteins listed in Table 1. In still other embodiments, the transgene is expressed such that a therapeutic protein product is released from the modified cell at some point, for example is released from a mature red blood cell that develops from a modified RBC precursor cell.

The invention also supplies methods and compositions for the production of an RBC carrier of a therapeutic protein that can be used universally for all subjects (e.g., human patients) as an allogenic product, for example, allowing the development of a single product for the treatment and/or prevention of subjects with genetic conditions and/or subjects likely to be exposed to toxins (e.g., nerve agents) and for treatment of victims of toxin (e.g., nerve agent) exposure.

In another aspect, the invention provides methods and compositions for the knock-out of regulatory genes whose products may inhibit expression of a gene in the RBC precursor, or the disruption of the target site on the DNA for such proteins. In some aspects, the genes or their target sequences chosen for knock-out are those involved in inhibiting the expression of fetal hemoglobin. RBCs differentiated from such precursors would contain fetal hemoglobin and could be used in subjects in low oxygen settings.

In another embodiment, the transgene encodes a non-coding RNA, e.g., an shRNA. Expression of the transgene prior to RBC maturation will result in a RBC containing the non-coding RNA of interest.

In another embodiment, the invention describes RBC precursor cells (i.e. hematopoietic stem cells: CD34+ cells) in which a transgene has been inserted such that mature RBCs derived from these precursors contain high levels of the product encoded by the transgene. In some embodiments, the precursors are induced pluripotent stem cells (iPSC). By way of non-limiting example only, genes that are highly expressed in iPSC-derived red blood cells are beta and gamma globin.

In some embodiments, the methods of the invention may be used in vivo, for example to generate transgenic animal systems. In some aspects, the transgenic animal may be used in model development where the transgene encodes a human gene. In some instances, the transgenic animal may be knocked out at the endogenous locus that encodes the inserted transgene, allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., globin or safe-harbor) into a stem cell (e.g., an embryonic stem cell, an induced pluripotent stem cell, a hepatic stem cell, etc.) or animal embryo obtained by any of the methods described herein, and then the embryo is implanted such that a live animal is born. The animal is then raised to sexual maturity and allowed to produce offspring wherein at least some of the offspring comprise the integrated transgene.

In a still further aspect, provided herein is a method for site specific integration of a nucleic acid sequence into an endogenous locus (e.g., globin gene) of a chromosome, for example into the chromosome of an embryo. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a zinc finger, TALE or CRISPR/Cas system nuclease that recognizes the site of integration in the target locus (e.g., globin locus), and (b) culturing the embryo to allow expression of the zinc finger, and/or TALE or CRISPR/Cas system nuclease, wherein a double stranded break introduced into the site of integration by the zinc finger, TALE or CRISPR/Cas system is repaired, via homologous recombination with the DNA vector, so as to integrate the nucleic acid sequence into the chromosome.

In any of the methods described herein, the polynucleotide encoding the zinc finger nuclease(s) and/or TALEN(s) or CRISPR/Cas system can comprise DNA, RNA or combinations thereof. In certain embodiments, the polynucleotide comprises a plasmid. In other embodiments, the polynucleotide encoding the nuclease comprises mRNA.

A kit, comprising the ZFPs and/or TALENs or CRISPR/Cas system of the invention, is also provided. The kit may comprise nucleic acids encoding the ZFPs, TALENs, or CRISPR/Cas system (e.g. RNA molecules or ZFP, TALEN or Cas encoding genes contained in a suitable expression vector and suitable CRISPR guide RNAs if needed), donor molecules, suitable host cells or cell lines, instructions for performing the methods of the invention, and the like.

These and other aspects will be readily apparent to the skilled artisan in light of disclosure as a whole.

DETAILED DESCRIPTION

Disclosed herein are methods and compositions for delivering a therapeutic biologic to the desired site within an organism. The invention describes the alteration of a red blood cell such that it produces high levels of the therapeutic. The introduction of a population of these altered RBCs into a patient will supply that needed protein. The transgene can encode a desired protein or non-coding RNA that is beneficial therapeutically in a patient in need thereof. Furthermore, the altered RBC can be derived from an O-precursor cell or a precursor cell genetically engineered to lack the A, B, Rh, and/or Kell blood group antigens, making it a nearly universal donor cell. Such a universal donor cell can be propagated to yield a population that can be manufactured for ready use at any time. The invention is useful for treating humans in need of a therapeutic biologic produced from a transgene, for example humans who may be, will be, or have been exposed to a toxin.

Thus, the methods and compositions of the invention can be used to express from a transgene therapeutically beneficial proteins from highly expressed loci in red blood cells. For example, the transgene can encode a protein lacking or not sufficiently functional in a subject with a genetic condition (e.g., lysosomal storage disease) and/or a protein capable of binding to and/or inactivating toxic or undesirable agents in the body following exposure to a toxin.

In addition, the transgene can be introduced into patient-derived cells, e.g. patient-derived induced pluripotent stem cells (iPSCs) or other types of stems cells (embryonic or hematopoietic) for use in eventual implantation in a subject in need thereof.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084 and U.S. Publication No. 20110301073.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 2007/0218528, 2008/0131962 and 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Red Blood Cells" (RBCs), or erythrocytes, are terminally differentiated cells derived from hematopoietic stem cells. They lack a nuclease and most cellular organelles. RBCs contain hemoglobin to carry oxygen from the lungs to the peripheral tissues. In fact, 33% of an individual RBC is hemoglobin. They also carry $CO_2$ produced by cells during metabolism out of the tissues and back to the lungs for release during exhale. RBCs are produced in the bone marrow in response to blood hypoxia which is mediated by release of erythropoietin (EPO) by the kidney. EPO causes an increase in the number of proerythroblasts and shortens the time required for full RBC maturation. After approximately 120 days, since the RBC do not contain a nucleus or any other regenerative capabilities, the cells are removed from circulation by either the phagocytic activities of macrophages in the liver, spleen and lymph nodes (~90%) or by hemolysis in the plasma (~10%). Following macrophage engulfment, chemical components of the RBC are broken down within vacuoles of the macrophages due to the action of lysosomal enzymes.

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental and/or companion animals such as rabbits, dogs, cats, rats, mice, and other animals. Accordingly, the term "subject" or "patient" as used herein means any mammalian patient or subject to which the altered RBCs (or stem cells) of the invention can be administered. Subjects of the present invention include those that have been exposed to one or more chemical toxins, including, for example, a nerve toxin.

Nucleases

Described herein are compositions, particularly nucleases, which are useful targeting a gene for the insertion of a transgene into RBCs. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains) or a CRISPR/Cas system utilizing an engineered single guide RNA).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG family (SEQ ID NO: 26), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site in a target locus (e.g., globin or safe harbor) is an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and *Ralstonia* (see Heuer et al (2007) *Applied and Environmental Microbiology* 73(13): 4379-4384); U.S. Pat. Nos. 8,420,782 and 8,440,431 and U.S. Patent Publication No. 20110301073.

In certain embodiments, the DNA binding domain comprises a zinc finger protein (e.g., a zinc finger protein that binds to a target site in a globin or safe-harbor gene). Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding or TALE domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453, 242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA domains (e.g., multi-fingered zinc finger proteins or TALE domains) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The DNA binding proteins described herein may include any combination of suitable linkers between the individual zinc fingers of the protein. In addition, enhancement of binding specificity for zinc finger binding domains has been described, for example, in co-owned WO 02/077227.

Selection of target sites; DNA-binding domains and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496 and U.S. Publication No. 20110301073.

In addition, as disclosed in these and other references, DNA-binding domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014, 275. Likewise, TALE DNA-binding domains have been fused to nuclease domains to create TALENs. See, e.g., U.S. Publication No. 20110301073.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 20070134796, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014,275. Expression of the nuclease may be under the control of a constitutive promoter or an inducible promoter, for example the galactokinase promoter which is activated (de-repressed) in the presence of raffinose and/or galactose and repressed in presence of glucose.

The CRISPR/Cas System

Compelling evidence has recently emerged for the existence of an RNA-mediated genome defense pathway in archaea and many bacteria that has been hypothesized to parallel the eukaryotic RNAi pathway (for reviews, see Godde and Bickerton, 2006. *J. Mol. Evol.* 62: 718-729; Lillestol et al., 2006. *Archaea* 2: 59-72; Makarova et al., 2006. *Biol. Direct* 1: 7.; Sorek et al., 2008. *Nat. Rev. Microbiol.* 6: 181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (Makarova et al., 2006. *Biol. Direct* 1: 7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system.

The primary products of the CRISPR loci appear to be short RNAs that contain the invader targeting sequences, and are termed guide RNAs or prokaryotic silencing RNAs (psiRNAs) based on their hypothesized role in the pathway (Makarova et al. (2006) *Biol. Direct* 1:7; Hale et al. (2008) *RNA* 14: 2572-2579). RNA analysis indicates that CRISPR locus transcripts are cleaved within the repeat sequences to release ~60- to 70-nt RNA intermediates that contain individual invader targeting sequences and flanking repeat fragments (Tang et al. (2002) *Proc. Natl. Acad. Sci.* 99: 7536-7541; Tang et al. (2005) *Mol. Microbiol.* 55:469-481; Lillestol et al. (2006) *Archaea* 2:59-72; Brouns et al. (2008) *Science* 321: 960-964; Hale et al. (2008) *RNA* 14:2572-2579). In the archaeon *Pyrococcus furiosus*, these intermediate RNAs are further processed to abundant, stable ~35- to 45-nt mature psiRNAs (Hale et al. (2008) *RNA* 14: 2572-2579).

Cas Proteins

"Cas1" polypeptide refers to CRISPR associated (Cas) protein1. Cas1 (COG1518 in the Clusters of Orthologous Group of proteins classification system) is the best marker of the CRISPR-associated systems (CASS). Based on phylogenetic comparisons, seven distinct versions of the CRISPR-associated immune system have been identified (CASS1-7).

Cas1 polypeptide used in the methods described herein can be any Cas1 polypeptide present in any prokaryote. In certain embodiments, a Cas1 polypeptide is a Cas1 polypeptide of an archaeal microorganism. In certain embodiments, a Cas1 polypeptide is a Cas1 polypeptide of a Euryarchaeota microorganism. In certain embodiments, a Cas1 polypeptide is a Cas1 polypeptide of a Crenarchaeota microorganism. In certain embodiments, a Cas1 polypeptide is a Cas1 polypeptide of a bacterium. In certain embodiments, a Cas1 polypeptide is a Cas1 polypeptide of a gram negative or gram positive bacteria. In certain embodiments, a Cas1 polypeptide is a Cas1 polypeptide of *Pseudomonas aeruginosa*. In certain embodiments, a Cas1 polypeptide is a Cas1 polypeptide of *Aquifex aeolicus*. In certain embodiments, a Cas1 polypeptide is a Cas1 polypeptide that is a member of one of CASS1-7. In certain embodiments, Cas1 polypeptide is a Cas1 polypeptide that is a member of CASS3. In certain embodiments, a Cas1 polypeptide is a Cas1 polypeptide that is a member of CASS7. In certain embodiments, a Cas1 polypeptide is a Cas1 polypeptide that is a member of CASS3 or CASS7.

In some embodiments, a Cas1 polypeptide is encoded by a nucleotide sequence provided in GenBank at, e.g., GeneID number: 2781520, 1006874, 9001811, 947228, 3169280, 2650014, 1175302, 3993120, 4380485, 906625, 3165126, 905808, 1454460, 1445886, 1485099, 4274010, 888506, 3169526, 997745, 897836, or 1193018 and/or an amino acid sequence exhibiting homology (e.g., greater than 80%, 90 to 99% including 91%, 92%, 93%, 94%, 95%, 96%, 97%, 98% or 99%) to the amino acids encoded by these polynucleotides and which polypeptides function as Cas1 polypeptides.

Cas6 is another Cas polypeptide, and the endoribonuclease activity is referred to herein as Cas6 endoribonuclease activity. Non-limiting examples of suitable Cas6 polypeptides are depicted at Genbank Accession No. AAL81255. A Cas6 polypeptide may be enriched, isolated, or purified from a microbe having a CRISPR locus and the cas (CRISPR-associated) locus, such as, but not limited to, *Pyrococcus furiosus*, or may be produced using recombinant techniques, or chemically or enzymatically synthesized using routine methods. In some aspects, a Cas6 polypeptide may be enriched, isolated, or purified from a microbe that does not have CRISPR loci. A Cas6 polypeptide may include a GhGxxxxxGhG (SEQ ID NO:27 motif (where "h" indicates a hydrophobic amino acid) near the C-terminus. An Arg or Lys may be, and often is, found within the central stretch of 5 amino acids. A Cas6 polypeptide contains at least one residue that may play a role in catalysis, or conservative substitution thereof. A Cas6 polypeptide may contain other residues which may also play a role in catalysis, or conservative substitution thereof. The residue(s) expected to play a role in catalysis may be located near the G-rich loop that contains the Cas6 signature motif in the 3D structure of the protein. Cas6 polypeptides may include domains present in the TIGRFAM database at accession numbers TIGR01877 and PF01881. The TIGRFAM database includes families of polypeptides for which function is conserved (Haft et al. (2003) Nucl. Acids Res. 31:371-373, Bateman and Haft (2002) Briefings Bioinformatics, 3:236-245, and Haft et al. (2005) PLoS Computational Biol. 1(6):e60).

Other examples of Cas6 polypeptides provided herein include those present in prokaryotic microbes having a CRISPR locus and a cas locus. Cas6 polypeptides can be easily identified in any microbe that includes a CRISPR locus. A coding region encoding a Cas6 polypeptide is typically in a cas locus located in close proximity to a CRISPR locus. Haft et al. (2005) *PLoS Computational Biol.* 1(6):e60) review the Cas protein family, and created rules for the identification of specific subtypes of the CRISPR/Cas system. Haft et al. describe the coding region encoding Cas6 polypeptides as being found in association with at least four separate CRISPR/Cas subtypes (Tneap, Hmari, Apern, and Mtube), and as typically being the cas coding region located most distal to the CRISPR locus. Cas6 polypeptides may be identified using the resources available at the JCVI Comprehensive Microbial Resource. Thus, Cas6 polypeptides that are useful in the methods described herein can be identified by the skilled person using routine methods.

Examples of prokaryotic microbes with known whole genomic sequences containing coding regions expected to encode a Cas6 polypeptide include *Thermotoga maritima* MSB8, *Campylobacter fetus* subsp. *fetus* 82-40, *Fusobacterium nucleatum* ATCC 25586, *Streptococcus thermophilus* LMG 18311, *Thermoanaerobacter tengcongensis* MB4(T), *Moorella thermoacetica* ATCC 39073, *Desulfitobacterium hafniense* Y 51, *Clostridium tetani* E88, *Clostridium perfringens* SM101, *Clostridium difficile* QCD-32g58, *Clostridium botulinum* Hall A Sanger, *Clostridium botulinum* F Langeland, *Clostridium botulinum* B1 strain Okra, *Clostridium botulinum* A3 strain Loch Maree, *Clostridium botulinum* A Hall, *Clostridium botulinum* A ATCC 19397, *Carboxydothermus hydrogenoformans* Z-2901, *Staphylococcus epidermidis* RP62A, *Thermus thermophilus* HB8, *Thermus thermophilus* HB27, Nostoc sp. PCC 7120, *Anabaena variabilis* ATCC 29413, *Synechococccus* sp. OS Type B prime, *Synechococccus* sp. OS Type A, *Porphyromonas gingivalis* W83, *Bacteroides fragilis* YCH46, *Bacteroides fragilis* NCTC9343, *Aquifex aeolicus* VF5, *Rubrobacter xylanophilus* DSM 9941, *Mycobacterium tuberculosis* H37Rv (lab strain), *Mycobacterium tuberculosis* CDC1551, *Mycobacterium bovis* subsp. *bovis* AF2122/97, *Frankia alni* ACN14a, *Thermoplasma volcanium* GSS1, *Picrophilus torridus* DSM 9790, *Thermococcus kodakarensis* KOD1, *Pyrococcus horikoshii shinkaj* OT3, *Pyrococcus furiosus* DSM 3638, *Pyrococcus abyssi* GES, *Methanosarcina barkeri fusaro*, *Methanosarcina acetivorans* C2A, *Methanococcoides burtonii* DSM 6242, *Methanococcus jannaschii* DSM2661, *Methanobacterium thermoautotrophicum* delta H, *Haloarcula marismortui* ATCC 43049, *Archaeoglobus fulgidus* DSM4304, *Pyrobaculum aerophilum* 1M2, *Sulfolobus tokodaii* strain 7, *Sulfolobus solfataricus* P2, *Sulfolobus acidocaldarius* DSM 639, *Aeropyrum pernix* K1. Other examples of Cas6 polypeptides are known to the skilled person, see, for instance, members of the COG1583 group of polypeptides (available at the Clusters of Orthologous Groups of proteins (COGs) web page through the National Center for Biotechnology Information internet site, see also Tatusov et al. (1997) *Science* 278:631-637 and Tatusov et al. (2003) BMC *Bioinformatics* 4(1):41), members of the InterPro family having accession number IPRO10156, Makarova et al. (2002) *Nuc. Acids Res.* 30:482-496 and Haft et al. (2005) *PLoS Comput. Biol.* 1(6):e60, 474-483).

There are three types of CRISPR/Cas systems which all incorporate RNAs and Cas proteins. Types I and III both have Cas endonucleases that process the pre-crRNAs, that, when fully processed into crRNAs, assemble a multi-Cas protein complex that is capable of cleaving nucleic acids that are complementary to the crRNA.

In type II CRISPR/Cas systems, crRNAs are produced using a different mechanism where a trans-activating RNA (tracrRNA) complementary to repeat sequences in the pre-crRNA, triggers processing by a double strand-specific RNase III in the presence of the Cas9 protein. Cas9 is then able to cleave a target DNA that is complementary to the mature crRNA however cleavage by Cas 9 is dependent both upon base-pairing between the crRNA and the target DNA, and on the presence of a short motif in the crRNA referred to as the PAM sequence (protospacer adjacent motif) (see Qi et al. (2013) *Cell* 152:1173). In addition, the tracrRNA must also be present as it base pairs with the crRNA at its 3' end, and this association triggers Cas9 activity.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand.

The requirement of the crRNA-tracrRNA complex can be avoided by use of an engineered "single-guide RNA" (sgRNA) that comprises the hairpin normally formed by the annealing of the crRNA and the tracrRNA (see Jinek et al. (2012) *Science* 337:816 and Cong et al. (2013) *Sciencexpress*/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam, ibid) and has been useful for zebrafish embryo genomic editing in vivo (see Hwang et al. (2013) *Nature Biotechnology* 31(3):227) with editing efficiencies similar to ZFNs and TALENs.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof.

"Cas polypeptide" encompasses a full-length Cas polypeptide, an enzymatically active fragment of a Cas polypeptide, and enzymatically active derivatives of a Cas polypeptide or fragment thereof. Suitable derivatives of a Cas polypeptide or a fragment thereof include but are not limited to mutants, fusions, covalent modifications of Cas protein or a fragment thereof.

Cas proteins and Cas polypeptides may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

The CRISPR/Cas system can also be used to inhibit gene expression. Lei et al. (2013) *Cell* 152(5):1173-1183) have shown that a catalytically dead Cas9 lacking endonuclease activity, when coexpressed with a guide RNA, generates a DNA recognition complex that can specifically interfere with transcriptional elongation, RNA polymerase binding, or transcription factor binding. This system, called CRISPR interference (CRISPRi), can efficiently repress expression of targeted genes.

Additionally, Cas proteins have been developed which comprise mutations in their cleavage domains to render them incapable of inducing a DSB, and instead introduce a nick into the target DNA ("Cas9 nicking enzyme", see Cong et al., ibid).

The Cas proteins of the invention may be mutated to alter functionality. Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227. Selection of target sites; DNA-binding domains and methods for design and construction of fusion proteins (and polynucleotides encoding same) are known to those of skill in the art and described in detail in U.S. Pat. Nos. 6,140,081; 5,789, 538; 6,453,242; 6,534,261; 5,925,523; 6,007,988; 6,013, 453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496 and U.S. Publication No. 20110301073.

RNA Components of CRISPR/Cas

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Chimeric or sgRNAs can be engineered to comprise a sequence complementary to any desired target. The RNAs comprise 22 bases of complementarity to a target and of the form G[n19], followed by a protospacer-adjacent motif (PAM) of the form NGG. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence that conforms to the G[n20]GG formula.

Target Sites

As described in detail above, DNA-binding domains can be engineered to bind to any sequence of choice in a locus, for example a globin or safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 20110301073.

Exemplary selection methods applicable to DNA-binding domains, including phage display and two-hybrid systems, are disclosed in U.S. Pat. Nos. 5,789,538; 5,925,523; 6,007, 988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Patent Publication No. 20110287512.

Donors

As noted above, insertion of an exogenous sequence (also called a "donor sequence" or "donor" or "transgene") is provided, for example for expression of a protein, correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Patent Publication Nos. 20100047805, 20110281361, 20110207221 and 20130326645. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into a globin locus such that some or none of the endogenous globin sequences are expressed, for example as a fusion with the transgene. In other embodiments, the transgene (e.g., with or without globin encoding sequences) is integrated into any endogenous locus, for example a safe-harbor locus. See, e.g., US patent publications 20080299580; 20080159996 and 201000218264.

When additional (e.g., globin) sequences (endogenous or part of the transgene) are expressed with the transgene, the additional sequences may be full-length sequences (wild-type or mutant) or partial sequences. Preferably the additional (e.g., globin) sequences are functional. Non-limiting examples of the function of these full length or partial globin sequences include increasing the serum half-life of the polypeptide expressed by the transgene (e.g., therapeutic gene) and/or acting as a carrier, causing secretion of the polypeptide from the host cell, or preventing alpha/beta globin chain imbalance and the resultant alpha-polymer toxicity to the RBC.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the exogenous sequence (donor) comprises a fusion of a protein of interest and, as its fusion partner, an extracellular domain of a membrane protein, causing the fusion protein to be located on the surface of the cell. This allows the protein encoded by the transgene to act in the serum of the subject when expressed on the surface of the RBC. In the case of treatment for exposure to an environmental toxin, the enzyme encoded by the transgene fusion on the surface of the RBC acts on the toxic compounds accumulating in the serum. In addition, if an RBC bearing an engineered, over-expressed protein is engulfed by a splenic macrophage, as is the normal course of RBC degradation, the lysosome formed when the macrophage engulfs the RBC will expose the membrane bound fusion protein or the cytosolic over-expressed protein to the abnormally high concentrations of toxic products/metabolic intermediates in the lysosome at the pH more naturally favorable to that enzyme. Non-limiting examples of potential fusion partners are shown below in Table 1.

TABLE 1

Examples of potential fusion partners

| Name | Activity |
|---|---|
| Band 3 | Anion transporter, makes up to 25% of the RBC membrane surface protein |
| Aquaporin 1 | water transporter |
| Glut1 | glucose and L-dehydroascorbic acid transporter |
| Kidd antigen protein | urea transporter |
| RhAG | gas transporter |
| ATP1A1, ATP1B1 | Na+/K+ - ATPase |
| ATP2B1, ATP2B2, ATP2B3, ATP2B4 | Ca2+ - ATPase |
| NKCC1, NKCC2 | Na+ K+ 2Cl- - cotransporter |

TABLE 1-continued

Examples of potential fusion partners

| Name | Activity |
|---|---|
| SLC12A3 | Na+—Cl- - cotransporter |
| SLC12A1, SLA12A2 | Na—K - cotransporter |
| KCC1 | K—Cl cotransporter |
| KCNN4 | Gardos Channel |
| Kell antigen | Blood cell marker |
| RHD | Ammonia transporter |
| Glycophorin A | Sialoglycoprotein in RBC membranes |

Furthermore, donors (transgenes) of the invention can include specific proteins capable of acting on, degrading and/or detoxifying a compound of interest. These proteins can be produced and held within the RBC such that toxin degradation occurs following diffusion of the toxin into the RBC while it is traveling through the blood stream. Alternatively, the protein (e.g., enzyme) can be anchored to the surface of the RBC where it will act on the toxin outside of the RBC in the serum. The protein may also be released or secreted into the blood stream by the RBC. Proteins that may be considered include those that degrade the toxin partially or fully such that it is no longer toxic. Other types of transgenes can be those that will sequester the compound (i.e. a heavy metal atom) until the RBC is removed from circulation. Multiple transgenes can be used in any combination.

Any gene product that blocks the function of a toxin (e.g., nerve agent) can be used. Non-limiting examples of gene products useful in degrading and/or blocking toxins include carboxylesterases (CaEs); antibodies; cholinesterases (ChEs) such as Butyrylcholinesterase (BCHE), fetal bovine serum AChE (FBS-AChE), equine serum butyrylcholinesterase (EqBChE); phosphotriesterases from *Pseudonomas diminuta* and/or Serum paraoxonase/arylesterase 1 (PON1), which can be engineered to degrade a broad spectrum of organophosphate nerve agents, peroxidases for degradation of BPAs, phytochelatins, which are metallothioneins for the detoxification of heavy metals.

In other embodiments, the transgene produces a product lacking or deficient in a subject with a lysosomal storage disease. In still further embodiments, the protein product produced treats, prevents and/or ameliorates the symptoms associated with the LSD. LSDs are a group of rare metabolic monogenic diseases characterized by the lack of functional individual lysosomal proteins normally involved in the breakdown of waste lipids, glycoproteins and mucopolysaccharides. See, e.g., Table 2. These diseases are characterized by a buildup of these compounds in the cell since it is unable to process them for recycling due to the mis-functioning of a specific enzyme. The most common examples are Gaucher's (glucocerebrosidase deficiency—gene name: GBA), Fabry's (α galactosidase deficiency—GLA), Hunter's (iduronate-2-sulfatase deficiency—IDS), Hurler's (alpha-L iduronidase deficiency—IDUA), and Niemann-Pick's (sphingomyelin phosphodiesterase 1 deficiency—SMPD1) diseases. See, U.S. patent application Ser. No. 13/839,336, incorporated by reference herein in its entirety.

Lysosomal storage diseases typically fall into five classes. These classes are shown below in Table 2 along with specific examples of the diseases. Thus, the donor molecules (transgenes) described herein can include sequences coding for one or more enzymes lacking or deficient in subjects with lysosomal storage diseases, including but not limited to the proteins shown in Table 2.

TABLE 2

Lysosomal Storage Diseases

| Protein | Disease | Disease Associated Gene | Accumulated product |
|---|---|---|---|
| 1. DEFECTS IN GLYCAN DEGRADATION | | | |
| I. Defects in glycoprotein degradation | | | |
| α-Sialidase (neuraminidase) | Sialidosis | NEU1 | sialidated glycopeptides and oligosaccharides |
| Cathepsin A | Galactosialidosis | CTSA | polysaccharide |
| lysosomal alpha-mannosidase | α-Mannosidosis | MAN2B1 | mannose-rich glycoproteins and oligosaccharides |
| lysosomal beta-mannosidase | β-Mannosidosis | MANBA | |
| Glycosylasparaginase | Aspartylglucosaminuria | AGA | glycoasparagines |
| Alpha L Fucosidase | Fucosidosis | FUCA1 | fucose |
| α-N-Acetylglucosaminidase | Sanfilippo syndrome B | NAGLU | glycosaminoglycan |
| II. Defects in glycolipid degradation | | | |
| A. GM1 Ganglioside | | | |
| β-Galactosidase | GM1 gangliosidosis/MPS IVB | GLB1 | keratan sulfate |
| β-Hexosaminidase α-subunit | GM2-gangliosidosis (Tay-Sachs) | HEXA | GM2 ganglioside |
| β-Hexosaminidase β-subunit | GM2-gangliosidosis (Sandhoff) | HEXB | GM2 ganglioside |
| GM2 activator protein | GM2 gangliosidosis | GM2A | GM2 ganglioside |
| Glucocerebrosidase | Gaucher disease | GBA | glucocerebroside |
| Saposin C | Gaucher disease (atypical) | PSAP | glucocerebroside |
| B. Defects in the degradation of sulfatide | | | |
| Arylsulfatase A | Metachromatic leukodystrophy | ARSA | sulphatide |
| Saposin B | Metachromatic leukodystrophy | PSAP | sulphatide |
| Formyl-Glycin generating enzyme | Multiple sulfatase deficiency | SUMF1 | sulfated lipids |

TABLE 2-continued

Lysosomal Storage Diseases

| Protein | Disease | Disease Associated Gene | Accumulated product |
|---|---|---|---|
| β-Galactosylceramidase (Krabbe) | Globoid cell leukodystrophy | GALC | galactocerebroside |

C. Defects in degradation of globotriaosylceramide

| | | | |
|---|---|---|---|
| α-Galactosidase A | Fabry | GLA | globotriaosylcera-mide |

III. Defects in degradation of Glycosaminoglycan (Mucopolysaccharidoses)
A. Degradation of heparan sulphate

| | | | |
|---|---|---|---|
| Iduronate sulfatase | MPS II (Hunter) | IDS | Dermatan sulfate, Heparan sulfate |
| Iduronidase | MPS 1 (Hurler, Scheie) | IDUA | Dermatan sulfate, Heparan sulfate |
| Heparan N-sulfatase | MPS IIIa (Sanfilippo A) | SGSH | Heparan sulfate |
| Acetyl-CoA transferase | MPS IIIc (Sanfilippo C) | HGSNAT | Heparan sulfate |
| N-acetyl glucosaminidase | MPS IIIb (Sanfilippo B) | NAGLU | Heparan sulfate |
| β-glucuronidase | MPS VII (Sly) | GUSB | |
| N-acetyl glucosamine 6-sulfatase | MPS IIId (Sanfilippo D) | GNS | Heparan sulfate |

B. Degradation of other mucopolysaccharides

| | | | |
|---|---|---|---|
| B-Galactosidase | MPS VIB (Morquio B) | GLB1 | Keratan sulfate, |
| Galactose 6-sulfatase | MPS IVA (Morquio A) | GALNS | Keratan sulfate, Chondroitin 6-sulfate |
| Hyaluronidase | MPS IX | HYAL1 | Hyaluronic acid |

C. Defects in degradation of glycogen

| | | | |
|---|---|---|---|
| α-Glucosidase | Pompe | GAA | Glycogen |

2. DEFECTS IN LIPID DEGRADATION
I. Defects in degradation of sphingomyelin

| | | | |
|---|---|---|---|
| Acid sphingomyelinase | Niemann Pick type A | SMPD1 | sphingomyelin |
| Acid ceramidase | Farber lipogranulomatosis | ASAH1 | nonsulfonated acid mucopolysaccharide |

II. Defects in degradation of triglycerides and cholesteryls ester

| | | | |
|---|---|---|---|
| Acid lipase | Wolman and cholesteryl ester storage disease | LIPA | cholesteryl esters |

3. DEFECTS IN PROTEIN DEGRADATION

| | | | |
|---|---|---|---|
| Cathepsin K | Pycnodystostosis | CTSK | |
| Tripeptidyl peptidase | Ceroide lipofuscinosis | PPT2 | |
| Palmitoyl-protein thioesterase | Ceroide lipofuscinosis | PPT1 | |

4. DEFECTS IN LYSOSOMAL TRANSPORTERS

| | | | |
|---|---|---|---|
| Cystinosin (cystin transport) | Cystinosis | CTNS | |
| Sialin (sialic acid transport) | Salla disease | SLC17A5 | N-acetylneuraminic acid |

5. DEFECTS IN LYSOSOMAL TRAFFICKING PROTEINS

| | | | |
|---|---|---|---|
| Phosphotransferase γ-subunit | Mucolipidosis III (I-cell) | GNPTG | |
| Mucolipin-1(cation channel) | Mucolipidosis | MCOLN1 | |
| LYSOSOME-ASSOCIATED MEMBRANE PROTEIN 2 | Danon | LAMP2 | |
| Niemann-Pick disease, type C1 | Niemann Pick type C | NPC1 | LDL cholesterol |
| palmitoyl-protein thioesterase-1 | Ceroid lipofuscinosis (Batten Disease) | CLN3 | autofluorescent lipopigment storage material |
| neuronal ceroid lipofuscinosis-6 | Ceroid lipofuscinosis 6 | CLN 6 | |
| neuronal ceroid lipofuscinosis-8 | Ceroid lipofuscinosis 8 | CLN 8 | |
| LYSOSOMAL TRAFFICKING REGULATOR | Chediak-Higashi | LYST | |
| Myocilin | Griscelli Type 1 | MYOC | |
| RAS-associated protein 27A | Griscelli Type 2 | RAB27A | |
| Melanophilin | Griscelli Type 3 | MLPH or MYO5A | |
| AP3 β-subunit | Hermansky Pudliak | AP3B1 | ceroid |

In some cases, the donor may be an endogenous gene that has been modified. Although antibody response to enzyme replacement therapy varies with respect to the specific therapeutic enzyme in question and with the individual patient, a significant immune response has been seen in many LSD patients being treated with enzyme replacement. In addition, the relevance of these antibodies to the efficacy of treatment is also variable (see Katherine Ponder, (2008) *J Clin Invest* 118(8):2686). Thus, the methods and compositions of the current invention can comprise the use of donor molecules whose sequence has been altered by functionally silent amino acid changes at sites known to be priming epitopes for endogenous immune responses, such that the polypeptide produced by such a donor is less immunogenic.

The methods and compositions of the invention may be used in conjunction with methods to increase the delivery of the therapeutic into the brain. There are some methods that cause a transient opening of the tight junctions between cells of the brain capillaries. Examples include transient osmotic disruption through the use of an intracarotid administration of a hypertonic mannitol solution, the use of focused ultrasound and the administration of a bradykinin analogue. Alternatively, therapeutics can be designed to utilize receptors or transport mechanisms for specific transport into the brain. Examples of specific receptors that may be used include the transferrin receptor, the insulin receptor or the low-density lipoprotein receptor related proteins 1 and 2 (LRP-1 and LRP-2). LRP is known to interact with a range of secreted proteins such as apoE, tPA, PAI-1 etc., and so fusing a recognition sequence from one of these proteins for LRP may facilitate transport of the enzyme into the brain, following expression in the RBC precursor of the therapeutic protein and secretion into the blood stream from the mature RBC (see Gabathuler, (2010) ibid).

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger, TALEN protein(s) and or a CRISPR/Cas system. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see, for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered nucleases and/or donors take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of nucleases and/or donors include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and pseudotyped AAV such as AAV2/8, AAV2/5 and AAV2/6 and the like, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions of the invention can be used in any circumstance wherein it is desired to supply a transgene encoding one or more therapeutics such that the therapeutic(s) is(are) produced in a RBC and/or hematopoietic stem cell such that mature RBCs derived from these cells contain the therapeutic.

Thus, the compositions and methods described herein can be used for degradation of a toxin in a subject wherein the subject has been exposed to a toxin, either through environmental exposure, an industrial accident, or through chemical warfare. Particularly useful with this technology is the expression of detoxifying enzymes either in or on a mature RBC that are capable of degrading nerve toxins following exposure to chemical warfare agents.

Additionally, the compositions and methods of the invention can be used to treat a genetic disease, for example a lysosomal storage disease. Therapeutic proteins may be expressed in a RBC precursor such that the mature RBCs contain the protein. Such RBCs are useful for treating a disease in which the normal expression of a protein is aberrant in a subject.

The following Examples relate to exemplary embodiments of the present disclosure in which the nuclease comprises a zinc finger nuclease (ZFN). It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains or TALENs and/or a CRISPR/Cas system comprising an engineered single guide RNA.

EXAMPLES

Example 1: Design, Construction and General Characterization of Zinc Finger Protein Nucleases (ZFNs)

Zinc finger proteins were designed and incorporated into plasmids, AAV or adenoviral vectors essentially as described in Urnov et al. (2005) Nature 435(7042):646-651, Perez et al (2008) *Nature Biotechnology* 26(7):808-816, and as described in U.S. Pat. No. 6,534,261. For ZFNs specific for the human beta globin locus and the human HPRT locus, and TALENs specific for the human HPRT locus, see U.S. Pat. No. 7,888,121 and U.S. Publication Nos. 2013122591 and 20130137104. For ZFNs specific for human AAVS1, see co-owned U.S. Pat. No. 8,110,379. For ZFNs specific for CCR5, see co-owned U.S. Pat. No. 7,951,925. For TALENs specific for AAVS1 and CCR5, see co-owned U.S. Patent Publication No. 20110301073. For ZFNs specific for mRosa, see co-owned U.S. Publication No. 20120017290, and for TALENs specific for mRosa, see U.S. Patent Publication No. 20110265198. For nucleases specific for albumin see PCT publication WO20130/3044008.

Example 2: Activity of Globin-Specific ZFNs

ZFN pairs targeting the human globin gene were used to test the ability of these ZFNs to induce DSBs at a specific target site. The amino acid sequences of the recognition helix region of the indicated ZFNs are shown below in Table 3 with their target sites (DNA target sites indicated in uppercase letters; non-contacted nucleotides indicated in lowercase). See, also, U.S. Patent Publication Nos. 20130137104 and 20130122591.

TABLE 3

Human beta globin specific zinc finger nucleases

| SBS# Target | F1 | F2 | F3 | F4 | F5 | F6 |
|---|---|---|---|---|---|---|
| 26755 GCAGTAACG GCAGAC (SEQ ID NO: 1) | DRSNLSR (SEQ ID NO: 3) | QSGDLTR (SEQ ID NO: 4) | RSDTLSQ (SEQ ID NO: 5) | QSGSLTR (SEQ ID NO: 6) | QNATRIK (SEQ ID NO: 7) | NA |
| 26758 GGGcAAGGT GAACGTG (SEQ ID NO: 2) | RSDSLSR (SEQ ID NO: 8) | DSSNRKT (SEQ ID NO: 9) | RSAALSR (SEQ ID NO: 10) | RLDNRTA (SEQ ID NO: 11) | RSSHLSR (SEQ ID NO: 12) | NA |
| 33501 GGAGAAGTC tGCCGTT (SEQ ID NO: 13) | TSGSLSR (SEQ ID NO: 15) | DRSDLSR (SEQ ID NO: 16) | DRSALAR (SEQ ID NO: 17) | QSSNLAR (SEQ ID NO: 18) | QSGHLSR (SEQ ID NO: 19) | NA |
| 33488 AGTCAGGTG CACCATGGT (SEQ ID NO: 14) | LRHHLTR (SEQ ID NO: 20) | LRHNLRA (SEQ ID NO: 21) | DQSNLRA (SEQ ID NO: 22) | RNASRTR (SEQ ID NO: 23) | RSDNLSE (SEQ ID NO: 24) | RSQHRKT (SEQ ID NO: 25) |

The Cel-I assay (Surveyor™, Transgenomics) as described in Perez et al, (2008) *Nat. Biotechnol.* 26: 808-816 and Guschin et al. (2010) *Methods Mol Biol.* 649:247-56), was used to detect ZFN-induced modifications. In this assay, PCR-amplification of the target site was followed by quantification of insertions and deletions (indels) using the mismatch detecting enzyme Cel-I (Yang et al. (2000) *Biochemistry* 39: 3533-3541) which provided a lower-limit estimate of DSB frequency. Three days following transfection of the ZFN expression vector at either standard conditions (37° C.) or using a hypothermic shock (30° C., see U.S. Patent Publication 20110041195), genomic DNA was isolated from K562 cells using the DNeasy kit (Qiagen).

The results from the Cel-I assay demonstrated that the ZFNs were capable of inducing cleavage at their respective target sites (see, also, U.S. Patent Publication No. 20130122591).

Example 3: Insertion of the BCHE Gene into the Beta Globin Locus

The ZFNs are used to introduce a donor DNA into the beta globin locus as follows. Donor DNAs are designed such that the sequence encoding the BCHE enzyme is flanked by sequences that are homologous (homology arms) to the region surrounding the ZFN cleavage site in the beta globin gene. The homology arms are approximately 500-600 base pairs in length. The BCHE donor sequence lacks any non-coding sequence such that when inserted into the beta globin target site, the expression of the donor is regulated by the beta globin promoter and any other beta globin regulatory sequences. When inserted, the BCHE donor is fused in frame with the endogenous globin sequences and results in a fusion protein, or alternatively, the BCHE donor is inserted such that expression of the donor from the beta globin promoter results in a protein which contains only BCHE encoded sequences.

To perform the insertion, initially a cell line such as K562 is used. The cells are treated with mRNAs encoding the ZFNs and then transduced with an adenoviral vector, and adeno-associated viral vector, a lentiviral vector, a plasmid, or single-stranded DNA comprising the BCHE donor.

For insertion into CD34+ cells, and subsequent differentiation into mature altered RBCs, the same ZFNs and donor constructs are used to target BCHE into the beta globin locus. The ZFNs are introduced into the cells as mRNA and the donors are introduced using methods known in the art (e.g. AAV or lentiviral vectors). Transductants are analyzed for gene insertion by performing PCR on the target region and performing the appropriate restriction analysis and/or sequence analysis to confirm insertion.

To differentiate the transgenic CD34+ cells into mature RBCs, methods known in the art are used. For example, SCD CD34+ cells are purified using Ficoll-Paque (GE Healthcare) and CD34+ microbeads (Miltenyi Biotec) according to the manufacturers' instructions. CD34+ cells are cultured in Iscove's MDM with BIT 95000 (StemCell Technologies) in the presence of growth factors. Cells are differentiated toward the erythroid lineage using a 2-phase liquid culture model. During the first 6 days (first phase), CD34+ cells are expanded with SCF (100 ng/ml), Flt3-L (100 ng/ml), and IL-3 (20 ng/ml). Expanded cells are then committed and differentiated toward the erythroid lineage (second phase) with Epo (2 U/ml) and SCF (50 ng/ml).

Example 4: Construction of a Red Blood Cell Pool for Treatment of a Population of Human Patients To develop an engineered red blood cell therapeutic, a donor encoding the transgene of choice (e.g., BCHE for blocking or degradation of a toxin or a therapeutic protein for a genetic condition such as LSD) is used to insert the transgene into a blood type O-negative hematopoietic stem cell (HSC) population. The nucleases (e.g., ZFNs, TALENs and/or CRISPR/Cas) targeted to an endogenous gene (e.g., globin, albumin, Rosa, AAVS1, CCR5, etc.) are introduced into the stem cells via RNA and the donor is transduced into the cells using any suitable delivery system, for example an adenoviral vector for ZFN and/or TALEN encoding sequences. Insertion of the donor into the target in the HSC is confirmed using PCR and/or sequence analysis. The cells are then differentiated into red blood cells using techniques known in the art, and are transfused (after pharmaceutical acceptable cell formulations are generated and/or following storage at appropriate conditions, for example freezing) into patients in need thereof, for example patients that have been or may be exposed to a nerve gas agent or patients with a genetic condition such as a LSD.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated modified type O negative (type O−) red blood cell (RBC) that secretes a protein that degrades or detoxifies one or more nerve agents, wherein the RBC is derived from a blood type O-negative population of RBC precursor cells comprising (i) a pair of zinc finger nucleases (ZFNs) that cleave an endogenous beta globin gene and (ii) a transgene comprising a sequence encoding the protein, wherein the transgene is integrated into the endogenous beta globin gene of the RBC precursor cell population following cleavage by the pair of ZFNs, and further wherein the transgene integrated into the endogenous beta globin gene is integrated into or between the target sites as shown in SEQ ID NO:1 and SEQ ID NO:2 or into or between the target sites as shown in SEQ ID NO:13 and SEQ ID NO:14, such that expression of the protein is driven by the endogenous promoter of the beta globin gene.

2. The RBC cell of claim 1, wherein the transgene is integrated into an endogenous beta globin gene such that the transgene is expressed as a fusion protein with polypeptides expressed from the endogenous beta globin gene.

3. The RBC cell of claim 2, wherein the polypeptides expressed from the endogenous beta globin gene are present on the amino (N)-terminal portion or carboxy (C)-terminal portion of the fusion protein.

4. The RBC cell of claim 1, wherein the cell expresses fetal hemoglobin.

5. The RBC according to claim 1 wherein the RBC lacks A, B, Rh, and/or Kell blood group antigens.

6. A method of degrading or detoxifying the effects of a nerve agent in a subject in need thereof, the method comprising administering a RBC according to claim 1 to the subject in need thereof.

* * * * *